United States Patent [19]

Weigert

[11] Patent Number: 4,820,883

[45] Date of Patent: Apr. 11, 1989

[54] DEFLUORINATION PROCESS USING ACTIVATED CARBON

[75] Inventor: Frank J. Weigert, Wilmington, Del.

[73] Assignee: E. I. Du Pont de Nemours and Company, Wilmington, Del.

[21] Appl. No.: 129,372

[22] Filed: Nov. 24, 1987

Related U.S. Application Data

[63] Continuation-in-part of Ser. No. 73,878, Jul. 13, 1987, abandoned, which is a continuation of Ser. No. 785,960, Oct. 10, 1985, abandoned.

[51] Int. Cl.$^4$ .................... C07C 17/24; C07C 17/34; C07C 21/18
[52] U.S. Cl. .................... 570/153; 570/132; 570/136
[58] Field of Search .................... 570/153

[56] References Cited

U.S. PATENT DOCUMENTS

| | | | |
|---|---|---|---|
| Re. 23,425 | 10/1951 | Harmon | 260/648 |
| 2,709,182 | 5/1955 | Farlow | 260/653 |
| 4,377,716 | 3/1983 | Anello et al. | 570/153 |
| 4,377,717 | 3/1983 | Anello et al. | 570/172 |

FOREIGN PATENT DOCUMENTS 766324  1/1957  United Kingdom ............... 570/153

OTHER PUBLICATIONS

Chambers et al., *J. C. S. Perkin I*, 1064 to 1067 (1981), and Chem. Comm. 475 and 476 (1978).

Ohsaka et al., *Chem, Abstracts 94*, 191660 (1981), Ger. Offen. 3,027,229).

Baciocchi, The Chemistry of Halides, Pseudo-Halides and Azides, (1983), 161-201.

*Primary Examiner*—J. E. Evans

[57] ABSTRACT

A method for preparing an unsaturated fluorocarbon by defluorinating a perfluoroalkene employing activated carbon.

9 Claims, No Drawings

DEFLUORINATION PROCESS USING ACTIVATED CARBON

This application is a continuation-in-part of application Ser. No. 073,878, filed July 13, 1987, now abandoned, which in turn is a continuation of application Ser. No. 785,960, filed Oct. 10, 1985, now abandoned.

BACKGROUND OF THE INVENTION

1. Field of the Invention

This invention concerns a method for defluorinating a perfluoroalkene to the corresponding more highly unsaturated fluorocarbon.

2. References

U.S. Pat. No. 4,377,717, issued to Anello, et al., on Mar. 22, 1983, discloses dimerization of hexafluoropropene to perfluoro-2-methylpentene-2 by heating at elevated temperatures in the presence of activated carbon.

Chambers, et al., *J.C.S. Perkin I*, 1064 to 1067 (1981), and *Chem. Comm.*, 475 and 476 (1978), describe defluorination of perfluorinated alkenes over platinum, iron, and cesium fluoride at elevated temperatures to give perfluorinated dienes and other products.

U.S. Pat. No. 2,709,182, issued to Farlow on May 24, 1955, discloses preparation of tetrafluoroethylene by a process wherein a fluorocarbon of at least three carbons and of a melting point no higher than 25° C. is pyrolyzed by heating at a temperature of at least 1500° C. Pyrolysis by passing the fluorocarbon between carbon electrodes is specifically disclosed.

U.S. Pat. No. 23,425, issued to Harmon on Oct. 30, 1951, discloses a process for making completely halogenated polyfluorohydrocarbons comprising heating at a temperature of at least 125° C. a completely halogenated ethylene of the formula $CX_2=CX_2$, wherein X is halogen and at least 2 of the halogens are fluorine. The use of activated charcoal in the process is disclosed.

Ohsaka, et al., *Chem. Abstracts* 94, 191660 (1981) (Ger. Offen. No. 3,027,229) disclose oligomerization of hexafluoropropene over an alkali fluoride on carbon or NiO catalyst. Specifically disclosed is the oligomerization of $C_3F_6$ over KF on carbon at 200° C. to give a mixture of dimer, trimer, and $C_9F_{16}$.

Baciocchi, in "The Chemistry of Halides, Pseudo-Halides and Azides", Patai and Rappoport editors, John Wiley & Sons, New York, 1983, Chapter 5, pages 161 to 201, has reviewed 1,2-dehalogenations and related reactions.

SUMMARY OF THE INVENTION

This invention provides a process for preparing a perfluoroalkene having at least six carbon atoms and at least two carbon-carbon double bonds comprising contacting the corresponding perfluoroalkene having at least one carbon-carbon double bond in which both olefinic carbon atoms are quaternary with activated carbon to defluorinate the perfluoroalkene, thereby forming the perfluoroalkene having at least two carbon-carbon double bonds.

DETAILED DESCRIPTION OF THE INVENTION

The products of the invention, perfluoroalkenes having at least two carbon-carbon double bonds, are useful as comonomers for preparation of fluorocarbon-containing polymers and as cross-linking agents in fluoropolymers. The instant process represents an improvement in prior art processes for preparing perfluoroalkadienes in that lower temperatures can be employed and expensive metals such as platinum are not required. In some cases, isomerization may accompany or precede defluorination. For example, if perfluoro-3-isopropyl-4-methyl-2-pentene is employed as a starting material, isomerization to perfluoro-2,4-dimethyl-3-ethyl-2-pentene precedes defluorination (see Example 1).

The starting materials for the process of the invention are perfluoroalkenes having at least six carbon atoms. Perfluoroalkenes suitable as starting materials have at least one carbon-carbon double bond in which both olefinic carbon atoms are quaternary. By "quaternary carbon atom" is meant one to which only carbon atoms are attached. Preferred reactants are perfluoroalkenes containing 6 to 14 carbon atoms, the perfluoroalkene having only one carbon-carbon double bond. If the starting perfluoroalkene has more than one requisite carbon-carbon double bond, then the product can have more than two double bonds.

Representative perfluoroalkenes suitable as starting materials for the process of this invention include:
Tetrakis(trifluoromethyl)ethylene,
Perfluoro-2,4-dimethyl-3-ethyl-2-pentene,
Perfluoro-3,4-dimethyl-3-hexene,
Perfluoro-3,4,5-trimethyl-3-heptene, and
Perfluoro-1,2-bis(cyclobutyl)cyclobutene.
Other useful reactants will suggest themselves to those skilled in the art upon reading this disclosure.

By "activated carbon" is meant an amorphous carbon having high adsorptivity for gases, vapors, and colloidal solids. Such activated carbons are typically formed from the carbon-source by heating to about 800° to 900° C. with steam or carbon dioxide to confer upon the carbon a porous internal structure. Any of the well-known activated carbons can be used in the practice of this invention as well as any carbons activated according to the disclosure provided herein or any of the techniques known in the art to improve carbon adsorptivity. Commercially available activated carbons useful in the process of this invention include those sold under the following trademarks: Darco ™, Nuchar ™, Columbia SBV ™, Columbia MBV ™, Columbia MBQ ™, Columbia JXC ™, Columbia CXC ™, Calgon PCB ™, and Barnaby Cheny NB ™. The source, grade, or form of the activated carbon is not critical. However, it is preferred to use granules to facilitate use in tubular reactors. The size of the granules is not critical but it is preferred to employ granules having an average mesh size of about 1/25 to ¼ of the reactor diameter.

In the process of the invention the perfluoroalkene is contacted with activated carbon at a temperature of from about 300° to about 500° C., preferably from about 350° to 450° C.

The process of this invention can be carried out readily in liquid or gas phase using well-known chemical engineering practice, which includes continuous, semi-continuous, or batch operations. The process is conveniently carried out at atmospheric pressure, although either higher or lower pressures can be employed. The type of reactor vessel used is not critical so long as it is able to withstand the temperatures and pressures employed. Reactor vessels of stainless steel are typically used although other materials such as nickel-based corrosion resistant alloys, such as Hastelloy ™ alloy and tantalum can be used. The activated carbon can be used in a fixed bed or a fluidized bed configuration.

Contact times can vary from fractions of a second to 2 hours or more. Contact time is not critical since appreciable defluorination occurs even with relatively short contact times. For example, in a continuous flow process, a contact time as short as about 0.1 sec can be employed. In a batch process, a contact time of about 2 hr or longer can be used. When a continuous flow process is employed, contact time is calculated using the following equation.

$$\text{Contact Time} = \frac{\text{Volume of Carbon (mL)}}{\text{Gas Flow Rates (mL/hr)}}$$

The invention is further illustrated by the following examples in which all parts and percentages are by weight and all degrees are Celsius unless otherwise noted. Unless otherwise specified, the activated carbon employed in the examples comprised 12 to 30 mesh (2.00 mm–600 μm) granules having a surface area of over 1000 $m^2/g$ (Calgon PCB ™) as determined by standard nitrogen adsorption methods.

EXAMPLE 1

Defluorination of Hexafluoropropene(HFP) Trimers

A 1 mL sample of mixed HFP trimers ($C_9F_{18}$), perfluoro-3-isopropyl-4-methyl-2-pentene and perfluoro-2,4-dimethyl-3-ethyl-2-pentene, was heated in a sealed vessel with 1 g of activated carbon at 400° for 2 hrs. The product was shown to contain three isomers of $C_9F_{16}$ by GC/MS and fluorine nmr. Detailed analysis of the GC/MS patterns suggested the structures A, B, and C for the three defluorinated products. C apparently resulted from cyclization of B.

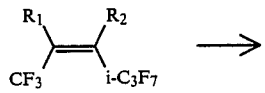

(1) $R_1 = F$; $R_2 = i-C_3F_7$
(2) $R_1 = CF_3$; $R_2 = C_2F_5$

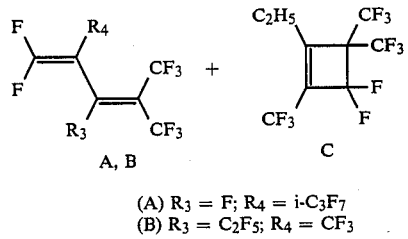

(A) $R_3 = F$; $R_4 = i-C_3F_7$
(B) $R_3 = C_2F_5$; $R_4 = CF_3$

EXAMPLE 2

Defluorination of Perfluoro-3,4-dimethyl-3-hexene

A mixture of 1 mL of perfluoro-3,4-dimethyl-3-hexene and 1 g of activated carbon was heated in a sealed vessel at 400° for 2 hr. The recovered carbon was extracted with chloroform, and the reaction product was identified as perfluoro-3,4-dimethyl-2,4-hexadiene by GC/MS and fluorine nmr spectrum.

EXAMPLE 3

Defluorination of Perfluoro-1,2-bis(cyclobutyl)-cyclobutene

A mixture of 1 mL of perfluoro-1,2bis(cyclobutyl)cyclobutene ($C_{12}F_{18}$) and 1 g of activated carbon was heated in a sealed vessel at 350° for 2 hr. The recovered carbon was extracted with chloroform, and the reaction product was shown to contain a mixture of several isomers of $C_{12}F_{16}$ and $C_{12}F_{14}$ by GC/MS.

EXAMPLE 4

Defluorination of Perfluoro-3,4,5-trimethyl-3-heptene

A mixture of 1 mL of perfluoro-3,4,5-trimethyl-3-heptene ($C_{10}F_{20}$) and 1 g of activated carbon was heated in a sealed vessel at 400° for 2 hr. The recovered carbon was extracted with chloroform, and the reaction product was identified as a mixture of several isomers of $C_{10}F_{18}$ by GC/MS.

The embodiments of the invention in which an exclusive property or privilege is claimed are defined as follows:

1. A process for preparing an unsaturated alipbatic or cycloaliphatic perfluorocarbon having at least six carbon atoms and having at least two carbon-carbon double bonds comprising contacting the corresponding unsaturated aliphatic or cycloaliphatic perfluorocarbon starting material having at least one carbon-carbon double bond in which both olefinic carbon atoms are quaternary with activated carbon at a temperature of from about 300° to about 500° C. to defluorinate said starting material, thereby forming the corresponding unsaturated aliphatic or cycloaliphatic perfluorocarbon having at least two carbon-carbon double bonds.

2. A process according to claim 1 wherein the starting material has from 6 to 14 carbon atoms.

3. A process according to claim 1 wherein the starting material is tetrakis(trifluoromethyl)-ethylene.

4. A process according to claim 1 wherein the starting material is perfluoro-2,4-dimethyl-3-ethyl-2-pentene.

5. A process according to claim 1 wherein the starting material is perfluoro-3,4-dimethyl-3-hexene.

6. A process according to claim 1 wherein the starting material is perfluoro-3,4,5-trimethyl-3-heptene.

7. A process according to claim 1 wherein the starting material is perfluoro-1,2-bis-(cyclobutyl)cyclobutene.

8. A process according to claim 1 wherein the temperature is from about 350° to about 450° C.

9. A process according to claim 8 wherein the activated carbon is in the form of granules.

* * * * *